(12) United States Patent
Jimenez et al.

(10) Patent No.: US 9,427,076 B2
(45) Date of Patent: *Aug. 30, 2016

(54) ORAL CARE SYSTEM, KIT AND METHOD

(71) Applicant: COLGATE-PALMOLIVE COMPANY, New York, NY (US)

(72) Inventors: Eduardo Jimenez, Manalapan, NJ (US); Alan Sorrentino, Cranbury, NJ (US); Robert Moskovich, East Brunswick, NJ (US)

(73) Assignee: COLGATE-PALMOLIVE COMPANY, New York, NY (US)

( * ) Notice: Subject to any disclaimer, the term of this patent is extended or adjusted under 35 U.S.C. 154(b) by 36 days.

This patent is subject to a terminal disclaimer.

(21) Appl. No.: 14/509,942

(22) Filed: Oct. 8, 2014

(65) Prior Publication Data
US 2015/0020333 A1  Jan. 22, 2015

Related U.S. Application Data

(63) Continuation of application No. 13/254,441, filed as application No. PCT/US2010/060877 on Dec. 16, 2010, now Pat. No. 8,882,380, which is a continuation-in-part of application No.
(Continued)

(51) Int. Cl.
*A46B 11/00* (2006.01)
*A61C 19/06* (2006.01)
(Continued)

(52) U.S. Cl.
CPC ........ *A46B 11/0024* (2013.01); *A46B 11/0027* (2013.01); *A46B 11/0034* (2013.01);
(Continued)

(58) Field of Classification Search
CPC .......... A46B 11/0024; A46B 11/0027; A46B 11/2234; A46B 11/0065; A46B 2200/1064
USPC ................ 401/118, 123–125, 154, 172–175
See application file for complete search history.

(56) References Cited

U.S. PATENT DOCUMENTS

| 64,732 A | 5/1867 | Wylie |
| 261,456 A | 7/1882 | Hoffman |

(Continued)

FOREIGN PATENT DOCUMENTS

| DE | 3832224 | 8/1989 |
| EP | 0 385 815 | 9/1990 |

(Continued)

OTHER PUBLICATIONS

International Search Report and Written Opinion in International Application No. PCT/US10/060105, mailed Aug. 30, 2011.
(Continued)

*Primary Examiner* — Mark A Laurenzi
*Assistant Examiner* — Bradley Oliver

(57) ABSTRACT

An oral care system comprising an oral care implement and dispenser containing a fluid detachably coupled to the oral care implement. In one embodiment, the dispenser includes a reservoir containing a fluid and an actuator for dispensing the fluid from the dispenser; and the dispenser is alterable between: (i) a storage state in which the dispenser is detachably coupled to the oral care implement and a mechanical interference between a portion of the actuator and a portion of the oral care implement prohibits actuation of the actuator; and (ii) an application state in which a user can actuate the actuator to dispense the fluid from the dispenser.

29 Claims, 10 Drawing Sheets

Related U.S. Application Data

PCT/US2009/069408, filed on Dec. 23, 2009, and a continuation-in-part of application No. PCT/US2009/069402, filed on Dec. 23, 2009.

(60) Provisional application No. 61/410,514, filed on Nov. 5, 2010, provisional application No. 61/423,397, filed on Dec. 15, 2010, provisional application No. 61/423,414, filed on Dec. 15, 2010, provisional application No. 61/423,435, filed on Dec. 15, 2010, provisional application No. 61/423,449, filed on Dec. 15, 2010.

(51) Int. Cl.
*A45D 40/04* (2006.01)
*A45D 34/04* (2006.01)

(52) U.S. Cl.
CPC ......... *A46B11/0065* (2013.01); *A61C 19/066* (2013.01); *A45D 34/04* (2013.01); *A45D 40/04* (2013.01); *A46B 2200/1066* (2013.01); *Y10T 29/49826* (2015.01)

(56) References Cited

U.S. PATENT DOCUMENTS

| | | |
|---|---|---|
| 1,244,324 A | 10/1917 | Hackley |
| 1,292,416 A | 1/1919 | Auld |
| 1,374,330 A * | 4/1921 | Stevenson ............ A46B 5/0095 132/311 |
| 1,546,516 A | 7/1925 | Smith |
| 1,555,064 A | 9/1925 | La Mothe |
| 1,668,511 A | 5/1928 | McLaughlin |
| 1,701,030 A | 2/1929 | Collins |
| 1,716,617 A * | 6/1929 | Brockelsby .......... A46B 11/001 132/311 |
| 1,746,474 A | 2/1930 | Hogner |
| 1,913,528 A | 6/1933 | White |
| 1,975,723 A | 10/1934 | Johnssen |
| D134,723 S | 1/1943 | Riksheim |
| 2,356,874 A | 8/1944 | Nageotte |
| 2,437,769 A | 3/1948 | Traylor |
| 2,445,571 A | 7/1948 | Fuston |
| 2,448,033 A | 8/1948 | Kruck |
| 2,521,882 A | 9/1950 | Swift et al. |
| 2,541,949 A | 2/1951 | Thacker et al. |
| 2,579,899 A | 12/1951 | Burrows |
| 2,637,060 A | 5/1953 | Cowan |
| 2,656,843 A * | 10/1953 | Boulicault ............. A45D 44/18 222/390 |
| 2,670,881 A | 3/1954 | Sjoblom |
| 2,676,568 A | 4/1954 | Maczynski |
| 2,718,299 A | 9/1955 | Atwater et al. |
| 2,771,858 A | 11/1956 | Cribbs et al. |
| 2,800,899 A | 7/1957 | Barron |
| 2,885,110 A | 5/1959 | Tregilgas |
| 2,885,116 A | 5/1959 | Tregilgas |
| 2,962,032 A | 11/1960 | Reuter |
| 3,108,687 A | 10/1963 | Dayton |
| 3,148,684 A | 9/1964 | Keeler |
| 3,181,539 A | 5/1965 | Aston |
| 3,187,758 A | 6/1965 | Eklund |
| 3,215,320 A | 11/1965 | Heisler et al. |
| 3,293,749 A | 12/1966 | George et al. |
| 3,296,642 A | 1/1967 | Aylott |
| 3,358,699 A | 12/1967 | Bau |
| 3,359,991 A | 12/1967 | Spatz |
| 3,359,992 A | 12/1967 | Cishek et al. |
| 3,378,176 A | 4/1968 | Snyder |
| 3,406,694 A | 10/1968 | Odence |
| 3,468,612 A | 9/1969 | Aston |
| 3,683,924 A | 8/1972 | Louie |
| 3,986,645 A | 10/1976 | Baldwin et al. |
| 4,023,580 A * | 5/1977 | Pieters .................. A45D 44/18 132/311 |
| 4,275,750 A | 6/1981 | Clark |
| 4,296,518 A | 10/1981 | Furrier et al. |
| 4,323,157 A | 4/1982 | Idec |
| 4,331,267 A | 5/1982 | Duncan et al. |
| 4,340,367 A | 7/1982 | Vadas et al. |
| 4,350,712 A | 9/1982 | Kocharian et al. |
| 4,384,645 A | 5/1983 | Manfredi |
| 4,413,760 A | 11/1983 | Paton |
| 4,506,810 A | 3/1985 | Goncalves |
| 4,527,574 A | 7/1985 | Manfredi |
| 4,582,059 A | 4/1986 | Tiwari |
| 4,641,766 A | 2/1987 | Vlasich |
| 4,655,372 A | 4/1987 | Ross et al. |
| 4,659,327 A | 4/1987 | Bennett et al. |
| 4,662,385 A | 5/1987 | Schefer |
| 4,763,815 A | 8/1988 | Von Schuckmann et al. |
| 4,767,032 A | 8/1988 | Smith |
| 4,776,717 A | 10/1988 | Iizuka et al. |
| 4,808,022 A | 2/1989 | Iizuka et al. |
| 4,811,445 A | 3/1989 | Lagieski et al. |
| 4,826,341 A | 5/1989 | Kwak |
| 4,874,117 A | 10/1989 | Kay et al. |
| 4,879,781 A | 11/1989 | Desimone |
| 4,886,186 A | 12/1989 | Andris |
| 4,887,924 A | 12/1989 | Green |
| 4,892,427 A | 1/1990 | Ford |
| D310,308 S | 9/1990 | Wolsey |
| 4,954,000 A | 9/1990 | Gueret |
| 4,957,125 A * | 9/1990 | Yaneza ................ A46B 11/001 132/309 |
| 4,997,299 A | 3/1991 | Ohba |
| 5,000,356 A | 3/1991 | Johnson et al. |
| 5,011,317 A | 4/1991 | Gueret |
| 5,016,782 A | 5/1991 | Pfanstiel |
| 5,018,892 A | 5/1991 | Krueckel et al. |
| 5,066,155 A | 11/1991 | English et al. |
| 5,156,479 A | 10/1992 | Iizuka |
| 5,199,807 A | 4/1993 | Uchida |
| 5,217,475 A | 6/1993 | Kuber |
| 5,234,136 A | 8/1993 | Kopis |
| 5,294,205 A | 3/1994 | Moeck et al. |
| 5,336,005 A | 8/1994 | Moeck et al. |
| 5,423,623 A | 6/1995 | Bakic |
| 5,540,361 A | 7/1996 | Fattori |
| 5,547,302 A | 8/1996 | Dornbusch et al. |
| 5,560,518 A | 10/1996 | Catterall et al. |
| 5,569,278 A | 10/1996 | Persad |
| 5,573,341 A | 11/1996 | Iaia |
| 5,697,531 A | 12/1997 | Fattori |
| 5,709,004 A | 1/1998 | Paduano et al. |
| 5,725,133 A | 3/1998 | Iaia |
| 5,765,573 A | 6/1998 | Gueret |
| 5,772,347 A | 6/1998 | Gueret |
| 5,803,640 A | 9/1998 | Nakajima et al. |
| 5,827,002 A | 10/1998 | Nakajima |
| 5,827,308 A | 10/1998 | Thakur et al. |
| 5,839,622 A | 11/1998 | Bicknell et al. |
| 5,851,079 A | 12/1998 | Horstman et al. |
| 5,860,572 A | 1/1999 | Harrold et al. |
| 5,879,095 A | 3/1999 | Gueret |
| 5,893,860 A | 4/1999 | Ripich et al. |
| 5,916,228 A | 6/1999 | Ripich et al. |
| 5,941,254 A | 8/1999 | Heler |
| 5,996,850 A | 12/1999 | Morali et al. |
| 6,015,293 A | 1/2000 | Rimkus |
| 6,039,053 A | 3/2000 | Turrentine |
| 6,056,763 A | 5/2000 | Parsons |
| 6,071,026 A | 6/2000 | Martinez et al. |
| 6,082,918 A | 7/2000 | Gueret |
| 6,086,276 A | 7/2000 | Gueret |
| 6,200,055 B1 | 3/2001 | Fusaro, Jr. |
| 6,202,247 B1 | 3/2001 | Lorenz, Jr. |
| 6,210,061 B1 | 4/2001 | Johnson |
| 6,213,662 B1 | 4/2001 | Aljanedi |
| 6,220,773 B1 | 4/2001 | Wiegner et al. |
| 6,224,573 B1 | 5/2001 | Yeager et al. |
| 6,227,209 B1 | 5/2001 | Kim et al. |
| 6,238,117 B1 | 5/2001 | Griebel et al. |
| 6,290,417 B1 | 9/2001 | Kaminski |
| 6,325,076 B1 | 12/2001 | Ramirez |

(56) References Cited

U.S. PATENT DOCUMENTS

| | | |
|---|---|---|
| 6,363,949 B1 | 4/2002 | Brown |
| 6,368,001 B1 | 4/2002 | Roeder |
| 6,398,439 B1 | 6/2002 | Szekely |
| 6,406,694 B1 | 6/2002 | LaRosa |
| 6,440,149 B1 | 8/2002 | Potti |
| 6,450,716 B1 | 9/2002 | Szekely |
| 6,475,172 B1 | 11/2002 | Hall |
| 6,647,581 B1 | 11/2003 | Persad et al. |
| 6,672,783 B1 | 1/2004 | Licata et al. |
| 6,688,317 B2 | 2/2004 | Gueret |
| 6,688,793 B2 | 2/2004 | Goyet |
| 6,688,796 B1 | 2/2004 | Liu |
| 6,745,781 B2 | 6/2004 | Gueret |
| 6,746,170 B2 | 6/2004 | Delage |
| 6,752,558 B1 | 6/2004 | Hsu |
| 6,824,018 B1 | 11/2004 | Eaddy et al. |
| 6,866,438 B2 | 3/2005 | Bauer et al. |
| 6,880,999 B2 | 4/2005 | Biegel et al. |
| 6,918,511 B1 | 7/2005 | Spatz et al. |
| 6,923,587 B2 | 8/2005 | Lee |
| 6,957,753 B2 | 10/2005 | Tani |
| 7,029,484 B2 | 4/2006 | Ripich |
| 7,044,671 B2 | 5/2006 | Parikh et al. |
| 7,051,642 B2 | 5/2006 | Kageyama |
| 7,055,527 B2 | 6/2006 | Tien |
| 7,086,564 B1 | 8/2006 | Corrigan |
| 7,086,796 B2 | 8/2006 | Severa |
| 7,089,564 B2 | 8/2006 | Chen et al. |
| 7,114,505 B2 | 10/2006 | Bauer et al. |
| 7,143,462 B2 | 12/2006 | Hohlbein |
| 7,144,175 B2 | 12/2006 | Biegel |
| 7,168,435 B2 | 1/2007 | Vieu et al. |
| 7,192,212 B2 | 3/2007 | Gutberlet et al. |
| 7,201,527 B2 | 4/2007 | Thorpe et al. |
| 7,217,054 B2 | 5/2007 | Noguchi |
| 7,226,231 B2 | 6/2007 | Py et al. |
| 7,237,974 B2 | 7/2007 | Pfenniger et al. |
| 7,237,975 B2 | 7/2007 | Noguchi |
| 7,303,348 B2 | 12/2007 | Phipps et al. |
| 7,309,184 B2 | 12/2007 | Butcher et al. |
| 7,309,185 B2 | 12/2007 | Thorpe et al. |
| 7,347,360 B2 | 3/2008 | Lasch et al. |
| 7,374,360 B1 | 5/2008 | Szekely |
| 7,396,180 B2 | 7/2008 | Bugla et al. |
| 7,401,373 B2 | 7/2008 | Tybinkowski et al. |
| 7,461,988 B2 | 12/2008 | Albisetti |
| 7,465,113 B2 | 12/2008 | Gueret |
| 7,474,048 B2 | 1/2009 | Forrest et al. |
| 7,520,406 B2 | 4/2009 | Jaichandra et al. |
| 7,557,936 B2 | 7/2009 | Dickinson |
| 7,614,811 B2 | 11/2009 | Kaufman et al. |
| 7,641,411 B2 | 1/2010 | Biegel |
| 7,651,291 B2 | 1/2010 | Py et al. |
| 7,665,923 B2 | 2/2010 | Py et al. |
| 7,975,341 B2 | 7/2011 | Cai et al. |
| 8,491,210 B2 * | 7/2013 | Jimenez .................. A46B 11/00 15/167.1 |
| 8,511,323 B2 | 8/2013 | Jimenez et al. |
| 8,523,475 B2 | 9/2013 | Jimenez et al. |
| 8,662,779 B2 | 3/2014 | deVirag et al. |
| 8,727,652 B2 | 5/2014 | Jimenez et al. |
| 8,882,380 B2 * | 11/2014 | Jimenez ............. A46B 11/0024 401/123 |
| 2002/0054783 A1 | 5/2002 | Gueret |
| 2002/0073496 A1 | 6/2002 | Kim |
| 2003/0057236 A1 | 3/2003 | Delage |
| 2004/0028456 A1 | 2/2004 | Giraldo |
| 2004/0092981 A1 | 5/2004 | Barlow et al. |
| 2005/0006409 A1 | 1/2005 | Ganzeboom |
| 2005/0026774 A1 | 2/2005 | Nolan |
| 2005/0036821 A1 * | 2/2005 | Pfenniger .......... A46B 15/0061 401/123 |
| 2005/0069372 A1 | 3/2005 | Hohlbein et al. |
| 2005/0135870 A1 | 6/2005 | Frison |
| 2006/0058821 A1 | 3/2006 | Jansheski |
| 2006/0207627 A1 | 9/2006 | Thorpe et al. |
| 2006/0233588 A1 | 10/2006 | Gueret |
| 2006/0269354 A1 | 11/2006 | Lane |
| 2006/0272666 A1 | 12/2006 | Wyatt et al. |
| 2006/0275225 A1 | 12/2006 | Prencipe et al. |
| 2007/0007302 A1 | 1/2007 | Jaichandra et al. |
| 2007/0079845 A1 | 4/2007 | Gueret |
| 2007/0227553 A1 | 10/2007 | Gueret |
| 2007/0231055 A1 | 10/2007 | Albisetti |
| 2007/0292194 A1 | 12/2007 | Albisetti et al. |
| 2008/0063464 A1 | 3/2008 | Prague |
| 2008/0089733 A1 | 4/2008 | Lochak |
| 2008/0101850 A1 | 5/2008 | Wojcik et al. |
| 2008/0189888 A1 | 8/2008 | Hohlbein |
| 2008/0274066 A1 | 11/2008 | Montgomery |
| 2009/0074679 A1 | 3/2009 | Silverman |
| 2009/0261007 A1 | 10/2009 | Sanchez |
| 2009/0317432 A1 | 12/2009 | Kergosien |
| 2010/0067969 A1 | 3/2010 | Kang |
| 2010/0296859 A1 * | 11/2010 | Lerner ............... A46B 11/0003 401/268 |
| 2011/0314623 A1 | 12/2011 | Jimenez et al. |
| 2012/0034016 A1 | 2/2012 | Jimenez et al. |
| 2012/0114410 A1 | 5/2012 | Jimenez et al. |
| 2012/0163902 A1 | 6/2012 | Jimenez et al. |
| 2012/0257920 A1 | 10/2012 | Jimenez et al. |
| 2012/0272996 A1 | 11/2012 | Jimenez et al. |
| 2012/0275841 A1 | 11/2012 | Jimenez et al. |
| 2012/0275843 A1 | 11/2012 | Jimenez et al. |
| 2013/0298341 A1 | 11/2013 | Jimenez et al. |
| 2013/0316300 A1 | 11/2013 | Jimenez et al. |

FOREIGN PATENT DOCUMENTS

| | | |
|---|---|---|
| EP | 1506726 | 2/2005 |
| FR | 850458 | 12/1939 |
| FR | 907669 | 3/1946 |
| FR | 1596074 | 6/1970 |
| FR | 2597734 | 10/1987 |
| GB | 2085717 | 5/1982 |
| GB | 2280361 | 2/1995 |
| GB | 2339384 | 1/2000 |
| JP | 48-093167 | 12/1973 |
| JP | 2003-009952 | 1/2003 |
| NL | 2002311 | 6/2010 |
| WO | WO 98/09572 | 3/1998 |
| WO | WO 01/00103 | 1/2001 |
| WO | WO 02/17967 | 3/2002 |
| WO | WO 2004/112637 | 12/2004 |
| WO | WO 2008/027999 | 3/2008 |
| WO | WO 2008/062935 | 5/2008 |
| WO | WO 2009/151455 | 12/2009 |

OTHER PUBLICATIONS

International Search Report and Written Opinion in International Application No. PCT/US10/060877, mailed Oct. 7, 2011.
International Search Report and Written Opinion in International Application No. PCT/US11/023356, mailed Oct. 21, 2011.
International Search Report and Written Opinion in International Application No. PCT/US10/60881 mailed May 16, 2011.
International Search Report and Written Opinion in International Application No. PCT/US09/069408 mailed Jul. 23, 2010.
International Search Report and Written Opinion in International Application No. PCT/US09/069402 mailed Jul. 23, 2010.
International Search Report and Written Opinion in International Application No. PCT/US10/060861 mailed Jun. 8, 2011.
International Search Report and Written Opinion in International Application No. PCT/US10/049102 mailed Jun. 7, 2011.

* cited by examiner

ORAL CARE SYSTEM, KIT AND METHOD

CROSS-REFERENCE TO RELATED APPLICATIONS

This application is a continuation of U.S. patent application Ser. No. 13/254,441, filed Sep. 1, 2011, now allowed, which is a national stage application of PCT/US2010/060877, filed on 16 Dec. 2010, which is a continuation in part of International Application No. PCT/US2009/069408 filed on Dec. 23, 2009 and International Application No. PCT/US2009/069402 filed on Dec. 23, 2009; which claim priority to U.S. Provisional Application No. 61/410,514 filed on Nov. 5, 2010; U.S. Provisional Application No. 61/423,397 filed on Dec. 15, 2010; U.S. Provisional Application No. 61/423,414 filed on Dec. 15, 2010; U.S. Provisional Application No. 61/423,435 filed on Dec. 15, 2010; and U.S. Provisional Application No. 61/423,449 filed on Dec. 15, 2010. The entirety of each of the foregoing applications is incorporated herein by reference.

FIELD OF THE INVENTION

The present invention relates generally to oral care systems, kits and methods, and more specifically to a system, kit and method including a toothbrush and a dispenser containing a fluid that detachably couples to the toothbrush.

BACKGROUND OF THE INVENTION

Oral care products or agents are applied in different ways. For example, without limitation, a common technique used for applying tooth whitening products is to cast an impression of a person's teeth and provide a tray of the shape of this impression. A person then only needs to add a whitening composition to the tray and apply the tray to his/her teeth. The tray is left in place for a period of time and then removed. After a few treatments the teeth gradually whiten. Another technique is to use a strip that has a whitening composition on one surface. This strip is applied to a person's teeth and left in place for about 30 minutes. After several applications the teeth are gradually whitened. Yet another technique is to apply a whitening composition to teeth using a small brush. This brush is repeatedly dipped back into the container during the application of the tooth whitening composition to one's teeth. After a few treatments the teeth gradually whiten.

A problem with existing brushing techniques is that saliva in the mouth contains the enzyme catalase. This enzyme will catalize the decomposition of peroxides. The brush can pick up some catalase during the application of some of the whitening product to teeth and transport that catalase back to the bottle. This catalase now in the bottle can degrade the peroxide in the bottle. Another problem with this latter technique is that it does not adapt for use with anhydrous whitening compositions. Here the brush may transport moisture from saliva from the mouth back into the bottle. This will have a negative effect on the whitening composition by potentially decomposing the peroxide active ingredient. In addition, if a person washes the brush each time after use, moisture from the wet bristles can enter the bottle.

While tray-based systems are suitable, many people do not use them due to the fact that they tend to be uncomfortable and/or awkward. Moreover, in order to use a whitening tray, a user must keep the tray and the required components at hand. This not only requires extra storage space in already cramped bathroom cabinets but also requires that the user remember to use the whitening system. Furthermore, these tray-based systems are not conveniently portable for transport and/or travel.

In addition to difficulties in applying some oral care products, storage is sometimes cumbersome and inconvenient for the user. The oral care product must typically be stored separately from oral care tooth cleaning implements such as a toothbrush since the oral care product package and toothbrush heretofore are generally treated as separate and distinct parts of an oral care regimen.

Further difficulties arise in that dispensers may be inadvertently activated to dispense the fluid prior to or after use due to unintentional manipulation of the actuator. This can be especially problematic if the dispenser is coupled to the oral care implement, which must be reused by the user over a period of time.

A more portable, compact and convenient way to store oral care products, and to dispense and apply those oral care products to oral surfaces is desired.

BRIEF SUMMARY OF THE INVENTION

Embodiments of the present invention provide an efficient, compact, and portable oral care system that combines an oral care implement, such as a toothbrush, with a fluid dispenser. Advantageously, certain embodiments are especially suited for easy transport and/or travel.

Exemplary embodiments of the present invention are directed to a toothbrush that detachably retains a removable dispenser containing a fluid reservoir. In some exemplary embodiments, the oral care system includes fluids, either active or non-active agents, that may include without limitation, whitening, enamel protection, anti-sensitivity, fluoride, tartar protection, or other fluidic materials. The dispenser can be detachably coupled to the toothbrush. In one embodiment, the dispenser may be at least partially located within the handle of the toothbrush so that a portion of the dispenser protrudes from the toothbrush. The dispenser can be completely removable from the toothbrush in certain embodiments so that the user can apply the fluid to his/her teeth with ease, and then re-couple the dispenser to the toothbrush for convenient storage. In certain embodiments, the dispenser may be a pen-like component.

In one embodiment, the invention can be an oral care system comprising: a toothbrush; a dispenser comprising a reservoir containing a fluid and a rotatable actuator for dispensing the fluid from the dispenser; and the dispenser alterable between: (i) a storage state in which the dispenser is detachably coupled to the toothbrush and a mechanical interference between a portion of the rotatable actuator and a portion of the toothbrush prohibits rotation of the rotatable actuator relative to the toothbrush; and (ii) an application state in which a user can rotate the rotatable actuator to dispense the fluid from the dispenser.

In another embodiment, the invention can be an oral care system comprising: a toothbrush comprising: a handle; an anti-rotation feature; and a head; a dispenser comprising: a housing having a reservoir containing a fluid; a dispensing orifice located at a distal end of the housing; a rotatable actuator having an anti-rotation feature, the rotatable actuator located at a proximal end of the housing, wherein upon rotation of the rotatable actuator relative to the housing, the fluid from the reservoir is dispensed via the dispensing orifice; and the dispenser alterable between: (i) a storage state in which the dispenser is detachably coupled to the toothbrush and the anti-rotation features of the toothbrush and the rotatable actuator mechanically mate to prohibit rotation of the rotatable actuator relative to the toothbrush; and (ii) an application state in which a user can rotate the rotatable actuator to dispense the fluid from the dispenser.

In yet another embodiment, the invention can be an oral care system comprising: a toothbrush; a dispenser comprising a reservoir containing a fluid and a rotatable actuator for dispensing the fluid from the dispenser; the dispenser alterable between: (i) a storage state in which the dispenser is detachably coupled to the toothbrush; and (ii) an application state in which the dispenser is separated from the toothbrush; and one of the toothbrush or the dispenser comprising a key and the other of the toothbrush or the dispenser comprising a recess, and wherein the key mates with the recess when the dispenser is in the storage state so as to prohibit rotation of the rotatable actuator relative to the toothbrush.

In certain exemplary embodiments, any suitable fluid may be used with embodiments and methods described herein according to the present invention. Accordingly, the oral care treatment system may be any type of system including without limitation tooth whitening, enamel protection, anti-sensitivity, fluoride, tartar protection/control, and others. The invention is expressly not limited to any particular type of oral care system or oral care material, unless specifically claimed.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The features of the exemplified embodiments will be described with reference to the following drawings in which like elements are labeled similarly. The present invention will become more fully understood from the detailed description and the accompanying drawings, wherein.

DETAILED DESCRIPTION OF THE INVENTION

Figure 1:
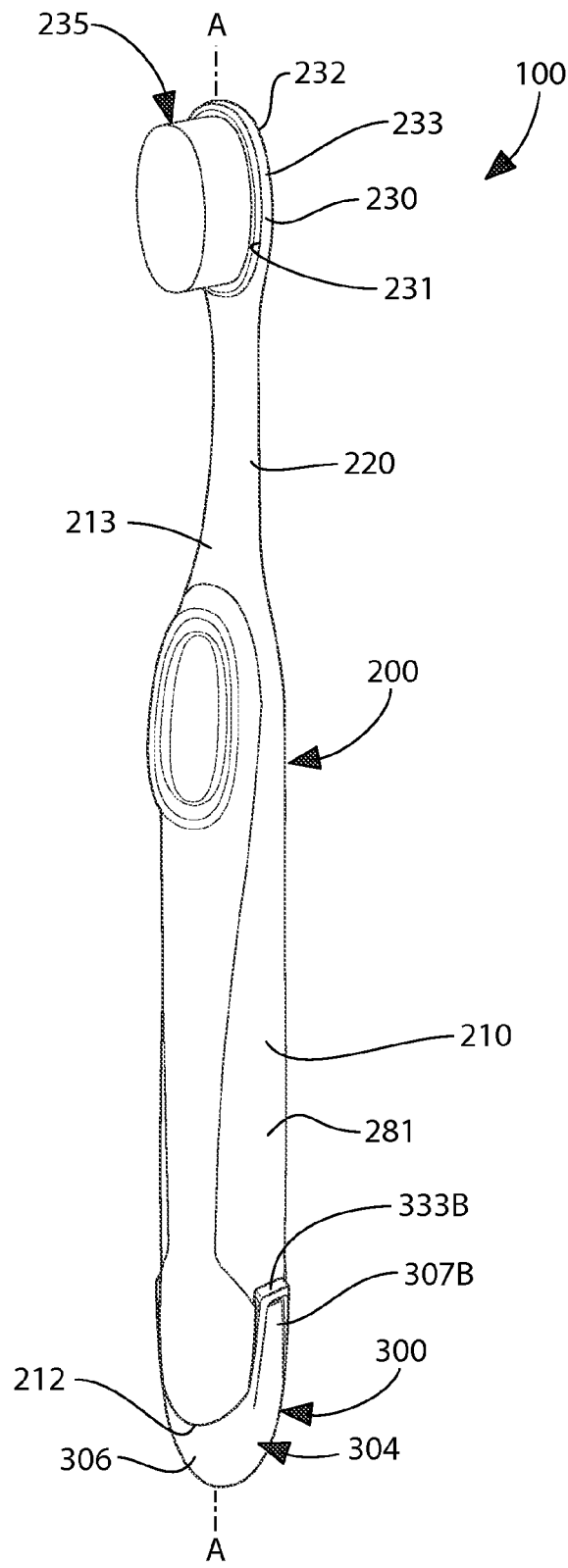
FIG. 1 is a front perspective view of an oral care system including a toothbrush and a fluid dispenser according to one embodiment of the present invention, wherein the dispenser is detachably coupled to the toothbrush.

The following description of the preferred embodiment(s) is merely exemplary in nature and is in no way intended to limit the invention, its application, or uses.

The description of illustrative embodiments according to principles of the present invention is intended to be read in connection with the accompanying drawings, which are to be considered part of the entire written description. In the description of embodiments of the invention disclosed herein, any reference to direction or orientation is merely intended for convenience of description and is not intended in any way to limit the scope of the present invention. Relative terms such as "lower," "upper," "horizontal," "vertical," "above," "below," "up," "down," "top" and "bottom" as well as derivative thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation unless explicitly indicated as such. Terms such as "attached," "affixed," "connected," "coupled," "interconnected," and similar refer to a relationship wherein structures are secured or attached to one another either directly or indirectly through intervening structures, as well as both movable or rigid attachments or relationships, unless expressly described otherwise. Moreover, the features and benefits of the invention are illustrated by reference to the exemplified embodiments. Accordingly, the invention expressly should not be limited to such exemplary embodiments illustrating some possible non-limiting combination of features that may exist alone or in other combinations of features; the scope of the invention being defined by the claims appended hereto.

Exemplary embodiments of the present invention will now be described with respect to one possible oral care system. Embodiments of the oral care system may include without limitation the following fluids: tooth whitening, antibacterial, enamel protection, anti-sensitivity, anti-inflammatory, anti-attachment, fluoride, tartar control/protection, flavorant, sensate, colorant and others. However, other embodiments of the present invention may be used to store and dispense any suitable type of fluid and the invention is expressly not limited to any particular oral care system or oral care material alone.

Referring to FIGS. 1-5, an oral care system 100 is illustrated according to one embodiment of the present invention. The oral care system 100 is a compact, readily portable, self-contained, user-friendly system that comprises all of the necessary components and chemistries necessary for a user to perform a desired oral care treatment routine. As will be described in greater detail below, the oral care system 100 in one exemplary embodiment comprises a modified toothbrush 200 having a removable dispenser 300 disposed at least partially within its handle 210. Because the dispenser 300 is located within the handle 210 of the toothbrush 200, the oral care system 100 is portable for travel, easy to use, and reduces the amount of required storage space. Furthermore, since the toothbrush 200 and dispenser 300 are housed together, the user is less likely to misplace the dispenser 300 and more inclined to maintain the oral treatment routine with the dispenser 300 since brushing will remind the user to simply detach and apply the contents of the dispenser 300.

As discussed above, the oral care system 100 generally comprises the toothbrush 200 and the dispenser 300. While the invention is described herein with respect to the use of a toothbrush as one of the two primary components of the oral care system 100, it is to be understood that other alternate oral care implements can be used within the scope of the invention, including tongue cleaners, tooth polishers and/or specially designed ansate implements having tooth engaging elements. In certain instances, the toothbrush 200 may include tooth engaging elements that are specifically designed to increase the effect of the oral care material in the dispenser on the teeth. For example, the tooth engaging elements may include elastomeric wiping elements that assist in removing stains from teeth and/or assist with forcing the oral care material into the tubules of the teeth. Moreover, while the toothbrush 200 is exemplified as a manual toothbrush, the toothbrush may be a powered toothbrush in certain embodiments of the invention. It is to be understood that the inventive system can be utilized for a variety of intended oral care needs by filling the dispenser 300 with any fluid, such as an oral care agent that achieves a desired oral effect. In one embodiment, the fluid is free of (i.e., is not) toothpaste as the dispenser 300 is intended to augment not supplant the brushing regimen. The fluid can be selected to complement a toothpaste formula, such as by coordinating flavors, colors, aesthetics, or active ingredients.

The toothbrush 200 generally comprises a handle 210, a neck 220 and a head 230. The handle 210 provides the user with a mechanism by which he/she can readily grip and manipulate the toothbrush 200. The handle 210 may be formed of many different shapes, sizes and materials and may be formed by a variety of manufacturing methods that are well-known to those skilled in the art. Preferably, the handle 210 can house the dispenser 300 therein as described in detail below. If desired, the handle 210 may include a suitable textured grip made of soft elastomeric material. The handle 210 can be a single or multi-part construction. The handle 210 extends from a proximal end 212 to a distal end 213 along a longitudinal axis A-A. A cavity 280 (FIG. 6) is formed within the handle 210. An opening 215 is provided at the proximal end 212 of the handle 210 that provides a passageway into the cavity through which the dispenser 300 can be inserted and retracted. While the opening 215 is located at the proximal end 212 of the handle 210 in the exemplified embodiment, the opening 215 may be located at other positions on the handle 210 in other embodiments of the invention. For example, the opening 215 may be located on a longitudinal surface of the handle 210 (e.g., the front surface, the rear surface and/or the side surfaces) and be elongated to provide sufficient access to the cavity 280.

The handle 210 transitions into the neck 220 at the distal end 213. While the neck 220 generally has a smaller transverse cross-sectional area than the handle 220, the invention is not so limited. Broadly speaking, the neck 220 is merely the transition region between the handle 210 and the head 230 and can conceptually be considered as a portion of the handle 210. In this manner, the head 230 is connected to the distal end 213 of the handle 210 (via the neck 220).

The head 230 and the handle 210 of the toothbrush 200 are formed as a single unitary structure using a molding, milling, machining or other suitable process. However, in other embodiments, the handle 210 and head 230 may be formed as separate components which are operably connected at a later stage of the manufacturing process by any suitable technique known in the art, including without limitation thermal or ultrasonic welding, a tight-fit assembly, a coupling sleeve, threaded engagement, adhesion, or fasteners. Whether the head 230 and handle 210 are of a unitary or multi-piece construction (including connection techniques) is not limiting of the present invention, unless specifically claimed. In some embodiments of the invention, the head 230 may be detachable (and replaceable) from the handle 210 using techniques known in the art.

The head 230 generally comprises a front surface 231, a rear surface 232 and a peripheral side surface 233 that extends between the front and rear surfaces 231, 232. The front surface 231 and the rear surface 232 of the head 230 can take on a wide variety of shapes and contours, none of which are limiting of the present invention. For example, the front and rear surfaces 231, 232 can be planar, contoured or combinations thereof. Moreover, if desired, the rear surface 232 may also comprise additional structures for oral cleaning or tooth engagement, such as a soft tissue cleaner or a tooth polishing structure. An example of a soft tissue cleaner is an elastomeric pad comprising a plurality of nubs and or ridges. An example of a tooth polishing structure can be an elastomeric element, such as a prophy cup(s) or elastomeric wipers. Furthermore, while the head 230 is normally widened relative to the neck 220 of the handle 210, it could in some constructions simply be a continuous extension or narrowing of the handle 210.

The front surface 231 of the head 230 comprises a collection of oral cleaning elements such as tooth engaging elements 235 extending therefrom for cleaning and/or polishing contact with an oral surface and/or interdental spaces. While the collection of tooth engaging elements 235 is suited for brushing teeth, the collection of tooth engaging elements 235 can also be used to polish teeth instead of or in addition to cleaning teeth. As used herein, the term "tooth engaging elements" is used in a generic sense to refer to any structure that can be used to clean, polish or wipe the teeth and/or soft oral tissue (e.g. tongue, cheek, gums, etc.) through relative surface contact. Common examples of "tooth engaging elements" include, without limitation, bristle tufts, filament bristles, fiber bristles, nylon bristles, spiral bristles, rubber bristles, elastomeric protrusions, flexible polymer protrusions, combinations thereof and/or structures containing such materials or combinations. Suitable elastomeric materials include any biocompatible resilient material suitable for uses in an oral hygiene apparatus. To provide optimum comfort as well as cleaning benefits, the elastomeric material of the tooth or soft tissue engaging elements has a hardness property in the range of A8 to A25 Shore hardness. One suitable elastomeric material is styrene-ethylene/butylene-styrene block copolymer (SEBS) manufactured by GLS Corporation. Nevertheless, SEBS material from other manufacturers or other materials within and outside the noted hardness range could be used.

The tooth engaging elements 235 of the present invention can be connected to the head 230 in any manner known in the art. For example, staples/anchors, in-mold tufting (IMT) or anchor free tufting (AFT) could be used to mount the cleaning elements/tooth engaging elements. In AFT, a plate or membrane is secured to the brush head such as by ultrasonic welding. The bristles extend through the plate or membrane. The free ends of the bristles on one side of the plate or membrane perform the cleaning function. The ends of the bristles on the other side of the plate or membrane are melted together by heat to be anchored in place. Any suitable form of cleaning elements may be used in the broad practice of this invention. Alternatively, the bristles could be mounted to tuft blocks or sections by extending through suitable openings in the tuft blocks so that the base of the bristles is mounted within or below the tuft block.

The toothbrush 200 and the dispenser 300 are non-unitary separate structures that are specially designed to be detachably coupled together when in an assembled state (referred to herein as a storage state) and completely isolated and separated from one another when in a disassembled state (referred to herein as an application state). The toothbrush 200 and the dispenser 300 are illustrated in the storage state in FIG. 1 and in the application state in FIG. 5. The dispenser 300 can be slidably manipulated and altered between the storage state (FIG. 1) in which the dispenser 300 is located (or docked) in the toothbrush handle 210 and the application state (FIG. 5) in which the dispenser 300 is removed from the handle 210 by the user as desired.

Figure 5:
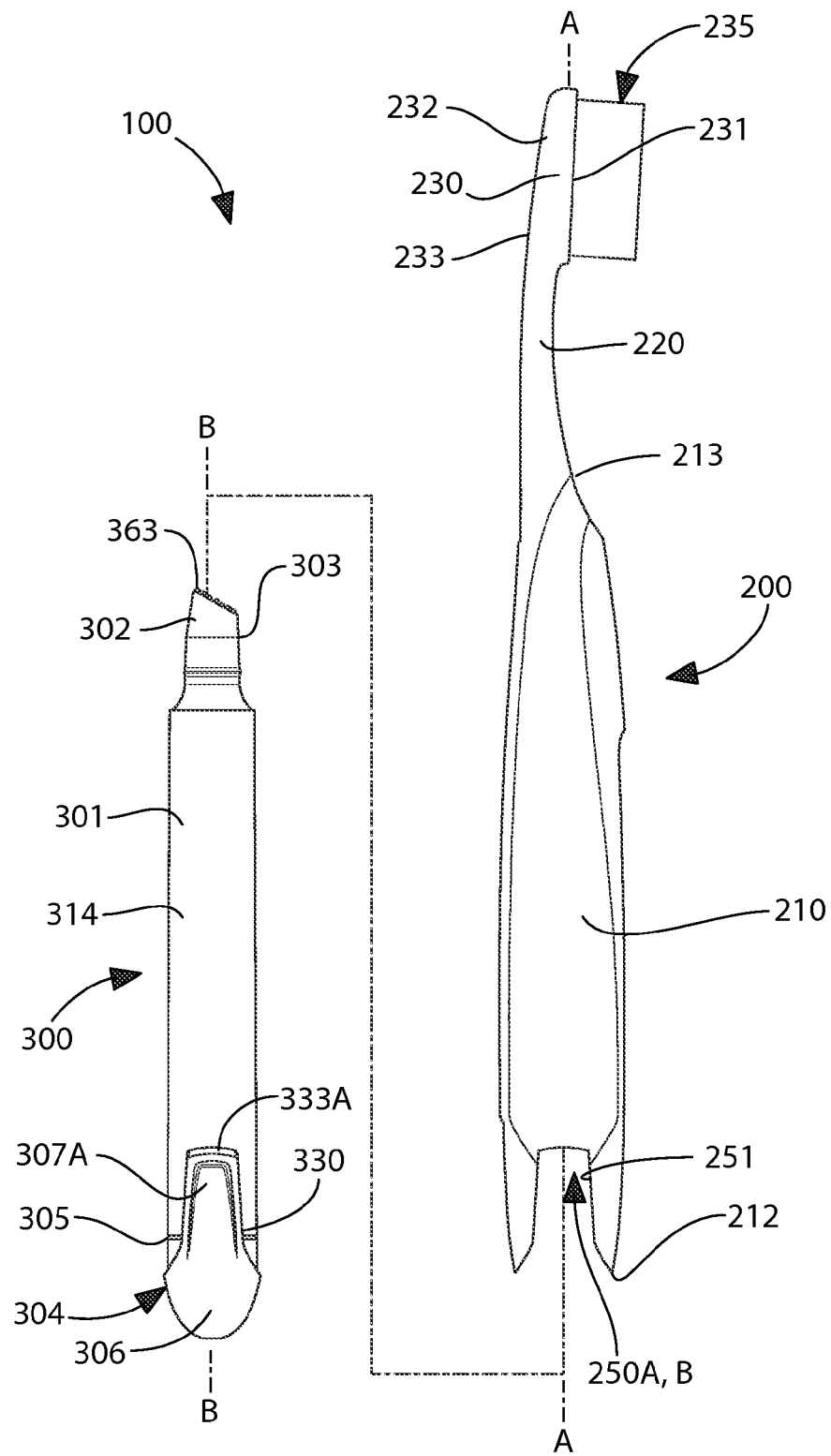
FIG. 5 is a left side view of the oral care system of FIG. 1, wherein the fluid dispenser is fully detached from the toothbrush and in an application state.
Figure 7:
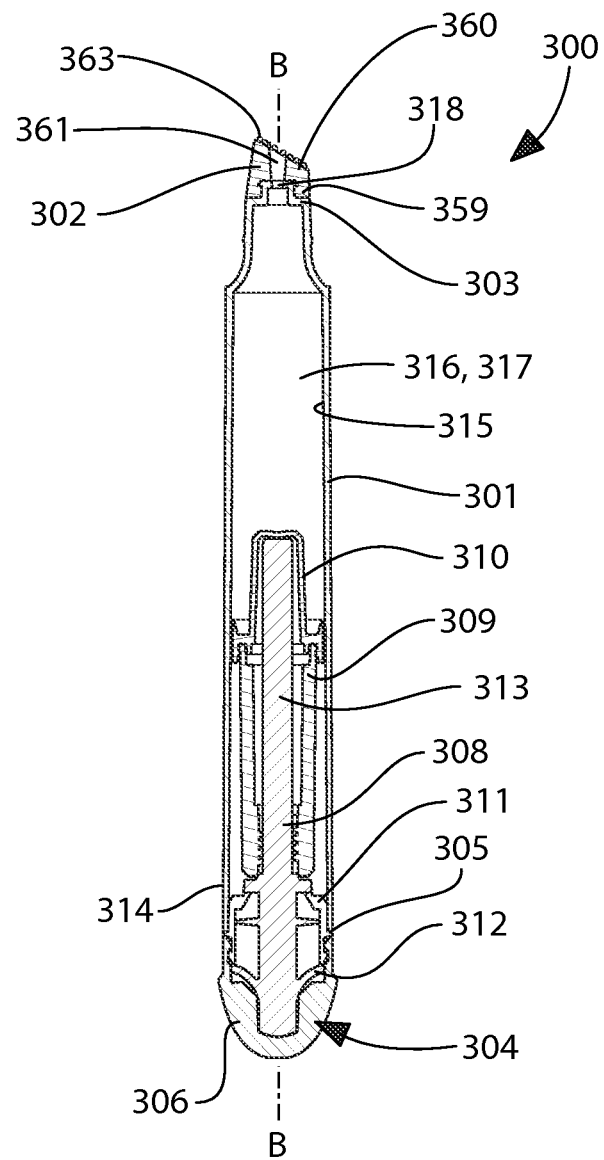
FIG. 7 is a longitudinal cross-sectional view of the fluid dispenser of the oral care system of FIG. 1.
Figure 8:
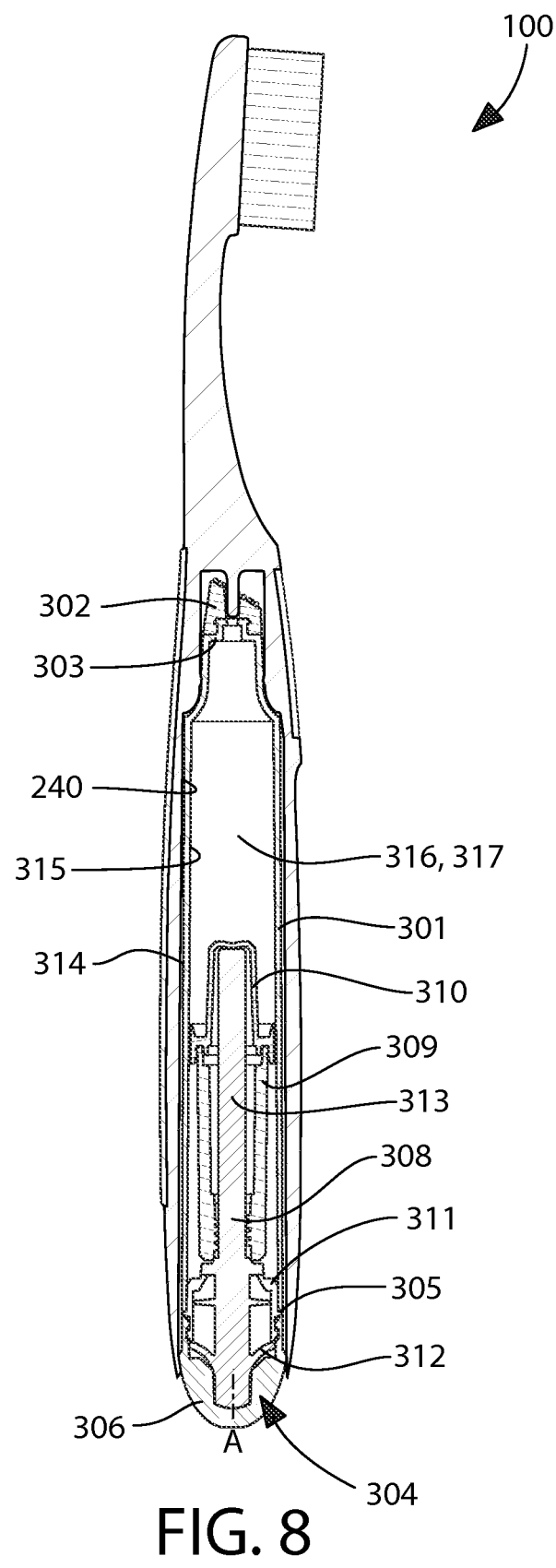
FIG. 8 is a longitudinal cross-sectional view of the oral care system of FIG. 1, wherein the fluid dispenser is detachably coupled to the toothbrush and in a storage state.

Referring now to FIGS. 5 and 7 concurrently, an embodiment of the dispenser 300 will be described in greater detail. Generally, the dispenser 300 is an elongated tubular pen-like structure that extends along a longitudinal axis B-B. The dispenser 300 generally comprises a housing 301, an applicator 302 located at a distal end 303 of the housing 301, and a rotatable actuator 304 located at a proximal end 305 of the housing 301. The dispenser 300 is designed so as to be capable of being operated to dispense the fluid stored therein using a single hand. Specifically, the dispenser 300 is positioned in a user's hand so that the rotatable actuator 304 is lodged in the palm of the user's hand. The user then uses the fingers of that same hand to rotate the housing 301 relative to the actuator 303. As a result, the fluid contained therein is dispensed from the dispenser 300.

Figure 4:
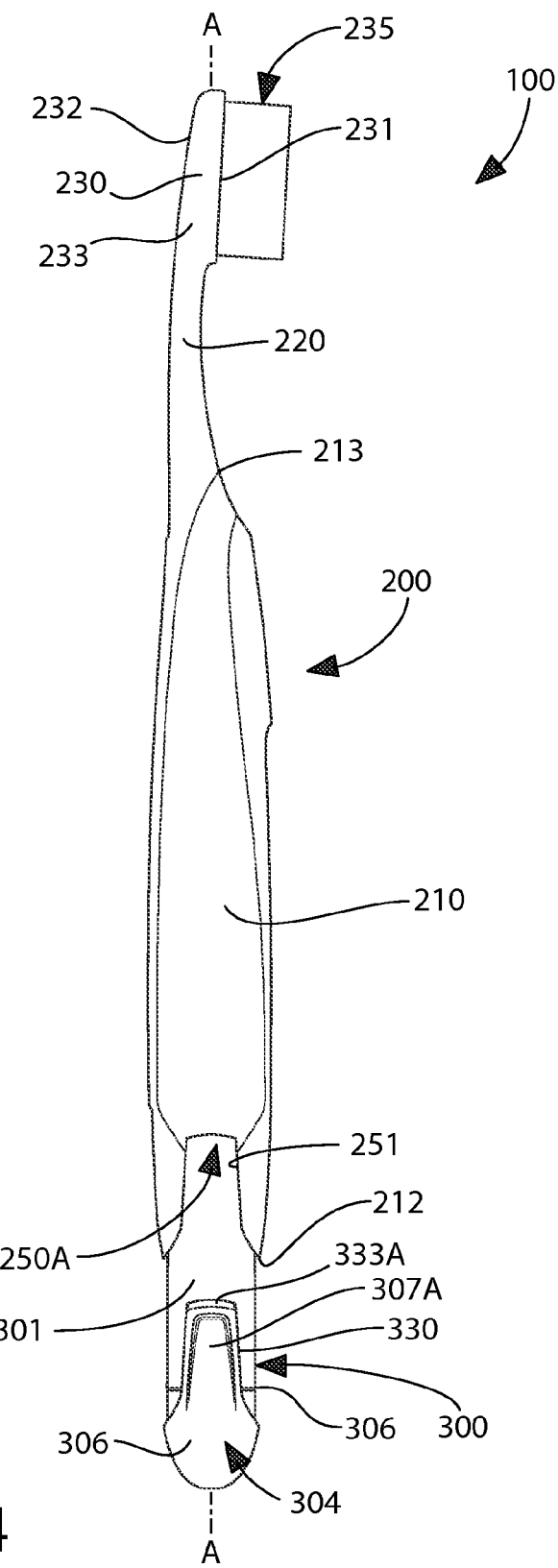
FIG. 4 is a left side view of the oral care system of FIG. 1, wherein the fluid dispenser is partially detached from the toothbrush.

In the exemplified embodiment, the housing 301 has a circular transverse cross-sectional profile (shown in FIGS. 4-5). Of course, in other embodiments, the transverse cross-sectional profile of the housing 301 can take on non-circular shapes. The housing 301 is constructed of a material that is sufficiently rigid to provide the necessary structural integrity for the dispenser 300. For example, the housing 301 can be formed of a moldable hard plastic. Suitable hard plastics include polymers and copolymers of ethylene, propylene, butadiene, vinyl compounds and polyesters such as polyethylene terephthalate. The chosen plastic(s), however, should be compatible with the fluid that is to be stored within the dispenser 300 and should not be corroded or degraded by the fluid.

While the housing 301 is exemplified as a single layer construction, in certain embodiments, the housing 301 may be a multilayer construction. In certain multi-layer embodiments, an inner layer can be formed from the hard plastic materials described immediately above while an outer layer can be formed of a soft resilient material, such as an elastomeric material. Suitable elastomeric materials include thermoplastic elastomers (TPE) or other similar materials used in oral care products. The elastomeric material of the outer layer may have a hardness durometer measurement ranging between A13 to A50 Shore hardness, although materials outside this range may be used. A suitable range of the hardness durometer rating is between A25 to A40 Shore hardness. While an over-molding construction is one suitable method of forming the outer layer, a suitable deformable thermoplastic material, such as TPE, may be formed in a thin layer and attached to inner layer with an appropriate adhesive, sonic welding, or by other means.

The housing 301 is an elongated hollow tubular structure extending along the longitudinal axis B-B from the proximal end 305 to the distal end 303. The housing 301 comprises an outer surface 314 and an inner surface 315 that forms an elongated internal cavity 316. As discussed in greater detail below, when the dispenser 300 is fully assembled, the internal cavity 316 of the housing 301 acts as a reservoir 317.

The reservoir 317 contains the desired fluid or product, which can be any active or inactive oral care agent. The oral care agent and/or its carrier may be in any form such as a solid or a flowable material including without limitation viscous pastes/gels or less viscous liquid compositions. The fluid is a flowable material having a low viscosity in certain embodiments. Any suitable fluid can be used in the present invention. For example, the fluid includes any oral care agents such as whitening agents, including without limitation, peroxide containing tooth whitening compositions. Suitable peroxide containing tooth whitening compositions are disclosed in U.S. Pat. Ser. No. 11/403,372, filed Apr. 13, 2006, to the present assignee, the entirety of which is hereby incorporated by reference. While a tooth whitening agent and a sensitivity agent are two of the exemplified active agents in the present invention, any other suitable oral care agents can be used with embodiments of the present invention and, thus, stored within the reservoir 317. Contemplated fluids are oral care agents that can be an active or non-active ingredient, including without limitation, antibacterial agents; oxidative or whitening agents; enamel strengthening or repair agents; tooth erosion preventing agents; anti-sensitivity ingredients; gum health actives; nutritional ingredients; tartar control or anti-stain ingredients; enzymes; sensate ingredients; flavors or flavor ingredients; breath freshening ingredients; oral malodor reducing agents; anti-attachment agents or sealants; diagnostic solutions; occluding agents; anti-inflammatory agents; dry mouth relief ingredients; catalysts to enhance the activity of any of these agents; colorants or aesthetic ingredients; and combinations thereof. The fluid in one embodiment is free of (i.e., is not) toothpaste. Instead, the active agent is intended to provide supplemental oral care benefits in addition to merely brushing one's teeth. Other suitable fluids could include lip balm or other materials that are typically available in a semi-solid state.

A dispensing orifice 318 is provided in the distal end 303 of the housing 301 through which fluid stored in the reservoir 317 can be dispensed from the dispenser 300. In the exemplified embodiment, the dispensing orifice 318 is located in a transverse end wall at the distal end 303 of the housing 301 and extends through the applicator 302. However, in certain embodiments, the dispensing orifice 318 will terminate at the applicator 302. In such embodiments, the fluid will be dispensed to the applicator 302 for subsequent application to the desired oral surface. Furthermore, in certain other embodiments, the dispensing orifice 318 can be located in other areas of the housing 301, such as on one of the longitudinal side walls. In some embodiments, a plurality of dispensing orifices 318 can be provided. For example, the plurality of dispensing orifices 318 can be provided in a generally circular configuration that may be used to facilitate the fluid being dispensed through the applicator 302.

The applicator 302, in the exemplified embodiment, is formed of a soft resilient material, such as an elastomeric material. Suitable elastomeric materials include thermoplastic elastomers (TPE) or other similar materials used in oral care products. The elastomeric material of the outer layer may have a hardness durometer measurement ranging between A13 to A50 Shore hardness, although materials outside this range may be used. A suitable range of the hardness durometer rating is between A25 to A40 Shore hardness.

In alternative embodiments, the applicator 302 may be constructed of bristles, a porous or sponge material, or a fibrillated material. Suitable bristles include any common bristle material such as nylon or PBT. The sponge-like materials can be of any common foam material such as urethane foams. The fibrillated surfaces can be comprised of various thermoplastics. The invention, however, is not so limited and the applicator 302 can be any type of surface and/or configuration that can apply a viscous substance onto the hard surface of teeth, including merely an uncovered opening/orifice.

The exemplary applicator 302 comprises a tubular sidewall 359 and a transverse end wall 360. An aperture 361 (which can be considered a portion of the dispensing orifice 318) is provided in the end wall 360 through which fluid from the reservoir 317 can be dispensed. A plurality of protuberances 363, such as nubs, extends from the outer surface of the end wall 360.

The actuator 304 protrudes axially from the proximal end 305 of the housing 301 so that a user can easily grip and rotate the actuator 304. The actuator 304 comprises a dome portion 306 and an anti-rotation feature, which in the exemplified embodiment is in the form of two members 307A, 307B that extend axially from the dome portion 306 toward the distal end 303 of the housing 301 and overlie a portion of the outer surface 314 of the housing 301. The anti-rotation feature of the rotatable actuator 304 of the dispenser 300 will be described in greater detail below. Moreover, it is to be understood that the rotatable actuator 304 can take on a wide variety of the structural shapes, such as a simple cylinder. In other embodiments, the rotatable actuator 304 can take on the shape of a gear with gear teeth.

In the exemplified embodiment, the rotatable actuator 304 is rotatable with respect to the housing 301 and also axially reciprocates along axis B-B during rotation. The exemplified internal dispensing subsystem of the dispenser 300 generally comprises a reciprocator 308, an extension member 309, an elevator 310, and a collar 311. The reciprocator 308 comprises the rotatable actuator 304, a resilient member 312 and a drive screw 313. The rotatable actuator 304 is rotatably coupled to the housing 301. Upon rotation of the rotatable actuator 304 relative to the housing 301, the elevator 310 is translated axially along the drive screw 313, thereby forcing the fluid from the reservoir 317 through the dispensing orifice 318 and to the applicator 302. While one embodiment of an internal dispensing subsystem is illustrated and described above, it is to be understood that a wide variety of mechanisms and subsystems can be used to dispense the fluid from the dispenser 300 in accordance with the present invention. The exact structural and functional details of the internal dispensing subsystem are not limiting of the present invention, unless specifically recited in the claims. It is to be understood that the present invention can be incorporated into any dispenser that utilizes a rotatable actuator as the mechanism to dispense the fluid from the dispenser, irrespective of the structural details and/or relative positioning of the rotatable actuator on the dispenser.

Figure 2:
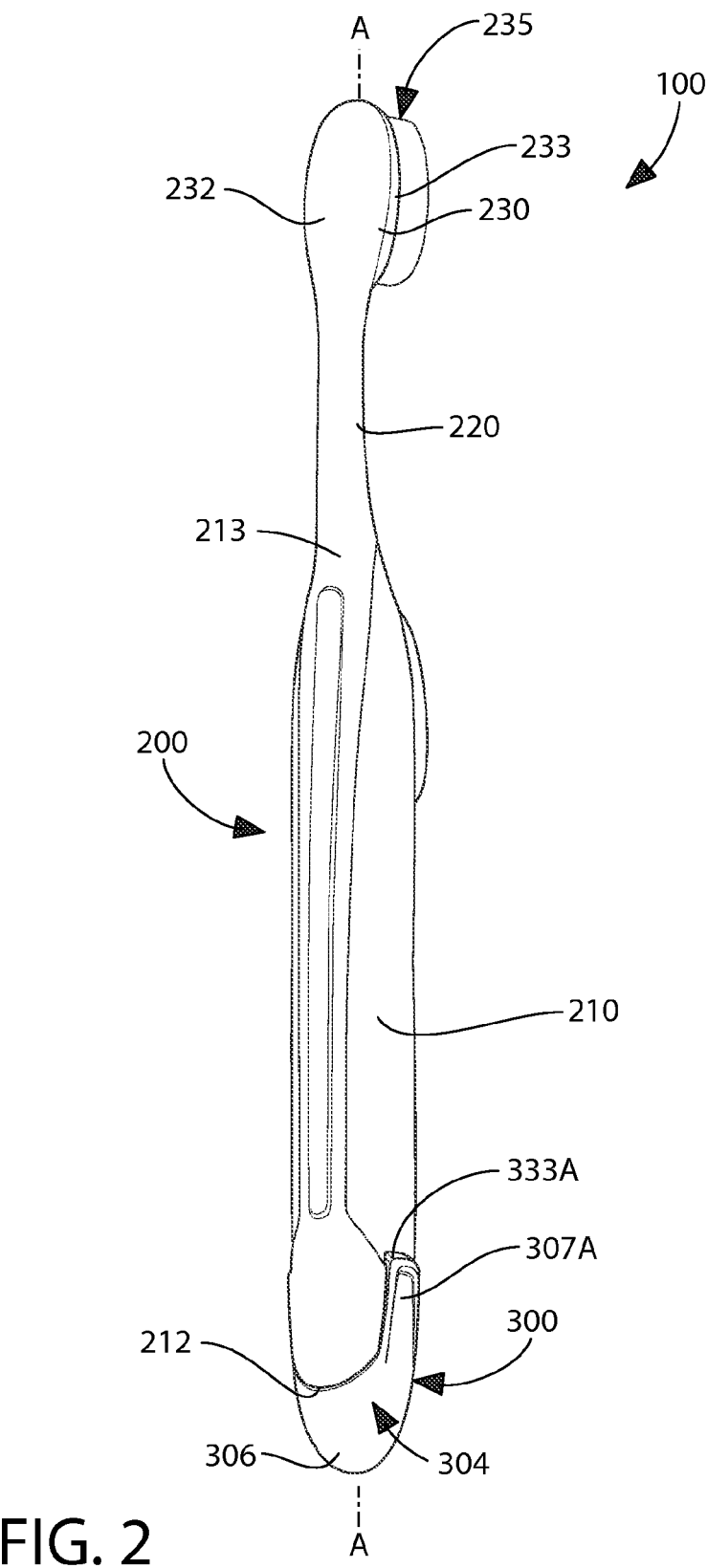
FIG. 2 is a rear perspective view of the oral care system of FIG. 1.
Figure 3:
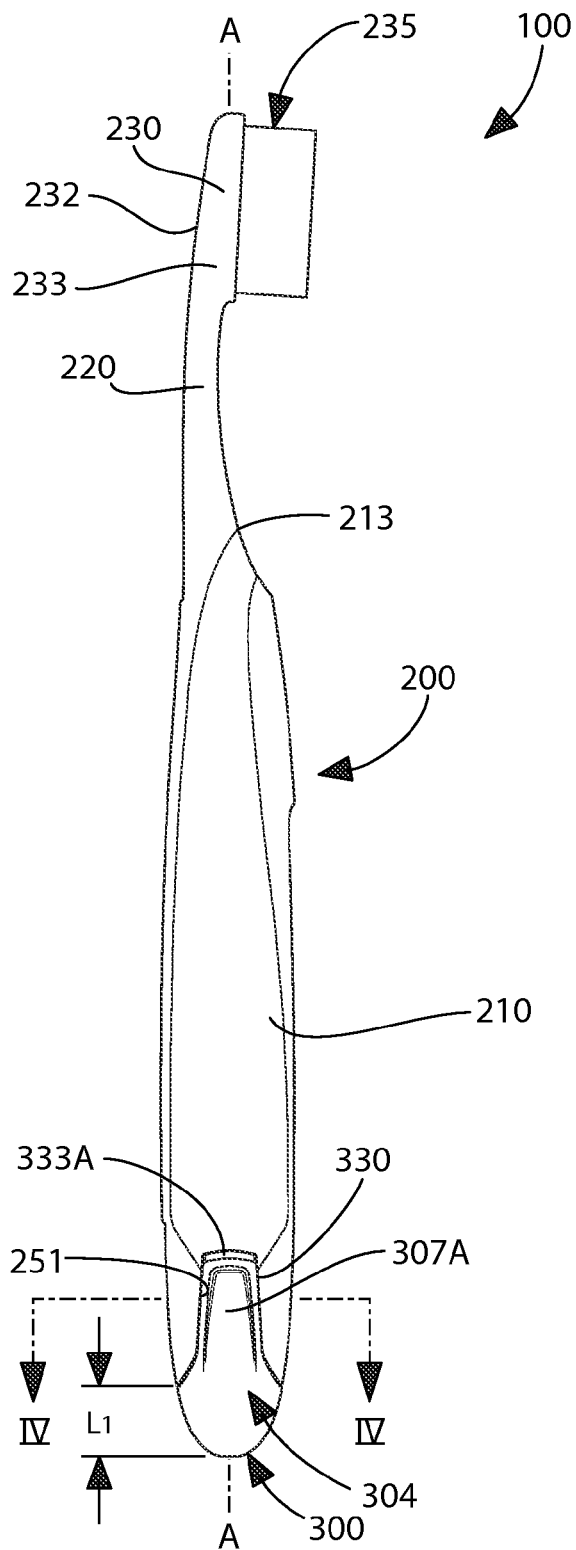
FIG. 3 is a left side view of the oral care system of FIG. 1.

Referring now to FIGS. 5 and 7 concurrently, when the dispenser 300 is in the application state (as illustrated), the rotatable actuator 304 of the dispenser 300 can be rotated to dispense the fluid from the dispenser 300. More specifically, when the dispenser 300 is in the application state, the rotatable actuator 304 of the dispenser 300 can be rotated with respect to the housing 301 to dispense the fluid from the dispenser 300. As a result, the user can use the dispenser 300 to apply the fluid directly to the desired oral surface. However, when the dispenser 300 is in the storage state (as shown in FIG. 1-3), it is desirable that the dispenser 300 be unable to dispense the fluid, which may occur due to inadvertent rotation of the rotatable actuator 304. Thus, as discussed below, the toothbrush 200 and the dispenser 300 are designed so that when the dispenser is in the storage state, the rotatable actuator 304 can not be rotated in a manner that would inadvertently dispense the fluid from the dispenser 300.

Figure 6:
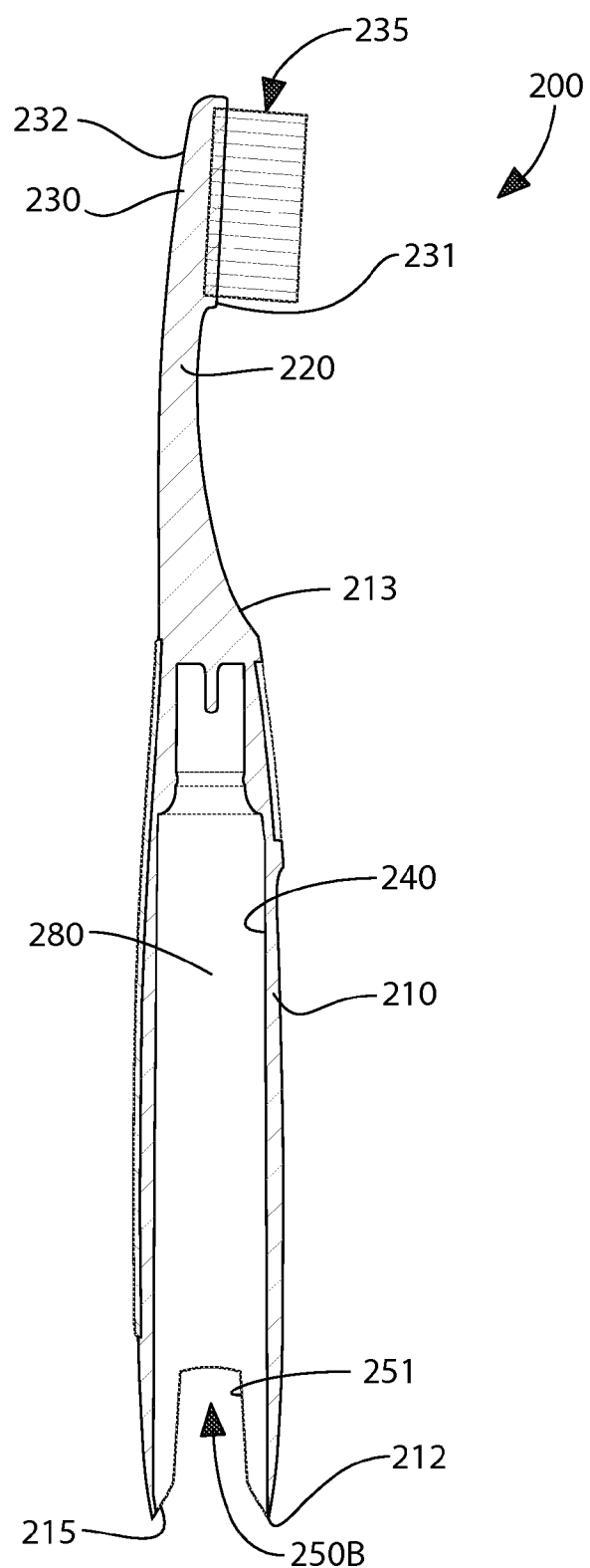
FIG. 6 is a longitudinal cross-sectional view of the toothbrush of the oral care system of FIG. 1.

Referring now to FIGS. 1, 3 and 6 concurrently, the dispenser 300 is illustrated in the storage state. When in the storage state, the dispenser 300 is docked within the cavity 280 of the handle 210 of the toothbrush 200. An interference fit between the outer surface 314 of the dispenser 300 and an inner surface 240 of the toothbrush 200 that forms the cavity 280 detachably couples the dispenser 300 to the toothbrush 200. When the dispenser 300 is in the storage state, at least a portion, and preferably a majority, of the dispenser 300 is located within the internal cavity 280 of the toothbrush 200.

In the exemplified embodiment, the entirety of the housing 301 of the dispenser 300, including the applicator 302, are located within the cavity 280 of the toothbrush 200 when the dispenser 300 is in the storage state. The rotatable actuator 304 of the dispenser, however, protrudes axially from the proximal end 212 of the handle 210 of the toothbrush 200. In this manner, the rotatable actuator 304 of the dispenser 300 forms a longitudinal extension $L_1$ of the handle 210 of the toothbrush 200. The dome portion 306 of the rotatable actuator 304 continues the natural contour of the handle 210 and provides a rounded proximal end to the oral care system 100, thereby providing a look that aesthetically resembles a traditional manual toothbrush.

While the housing 301 of the dispenser 300 is located within the cavity 280 of the toothbrush 200 and the rotatable actuator 304 protrudes from the handle 210 of the toothbrush 200, the rotatable actuator 304 can not be rotated relative to the toothbrush 200 (or relative to the housing 301 of the dispenser 300) due to a mechanical interference created between the anti-rotation feature of the rotatable actuator 304 and the anti-rotation feature of the toothbrush 200. In the exemplified embodiment, the anti-rotation feature of the rotatable actuator 304 comprises the two members 307A, 307B that extend from the dome portion 306 while the anti-rotation feature of the toothbrush 200 comprises two recesses 250A, 250B that are formed into a proximal edge 251 of the handle 210 of the toothbrush 200. It is understood that in other embodiments, the rotatable actuator 304 can be provided at different location with respect to the toothbrush 200. In such embodiments, different anti-rotation feature will be provided such that the rotatable actuator 304 can not be rotated relative to the toothbrush 200 (or relative to the housing 301 of the dispenser 300) in the storage state.

Referring now to FIGS. 3-5 and 9 concurrently, the structure and structural cooperation of the oral care system 100 that prohibits rotation of the rotatable actuator 304 when the dispenser is in the storage state will be described in greater detail.

As mentioned above, the rotatable actuator 304 comprises the dome portion 306 and the members 307A, 307B that extend axially therefrom and overlie the housing 301. The members 307A, 307B are non-rotatable relative to the dome portion 306. However, similar to the dome portion 306, the members 307A, 307B are rotatable relative to the housing 301 of the dispenser 300. The rotatable actuator 304 terminates in a distal edge 330 that is formed, in part, by the edges of the members 307A, 307B and the edges of the dome portion 306. In the exemplified embodiment, the distal edge 330 of the rotatable actuator 304 is a circumferentially undulating edge. However, the invention is not limited and, in other embodiments, can take on a wide variety of contours and/or arrangements.

As also discussed above, an opening 215 is provided at the proximal end 212 of the handle 210 of the toothbrush 200 that forms a passageway into the cavity 280. The opening 215 is defined by the proximal edge 251 of the handle 210. Two recesses 250A, 250B are formed in the proximal edge 251 and provide a geometry in which the members 307A, 307B of the rotatable actuator 304 can nest. When the dispenser 300 is fully inserted into the handle 210 so as to be in the storage state (FIGS. 3, 4 and 9), the members 307A, 307B of the rotatable actuator 304 slide into and nest within the recesses 250A, 250B of the toothbrush 200 respectively, thereby achieving a mating between the members 307A, 307B of the rotatable actuator 304 and the recesses 250A, 250B of the toothbrush 200 that prohibit the rotatable actuator 304 from being rotated relative to the toothbrush 200.

Conceptually, a keyed cooperation (best shown in FIG. 9) is created between the members 307A, 307B of the rotatable actuator 304 and the recesses 250A, 250B of the toothbrush 200 that prohibits relative rotation between the rotatable actuator 304 and the toothbrush 200. In the exemplified embodiment, the members 307A, 307B of the rotatable actuator 304 are the keys while the recesses 250A, 250B of the toothbrush 200 are the corresponding slots that mate with the keys. As a result of the aforementioned mechanical interference (or keyed cooperation), the rotatable actuator 304 can not be inadvertently rotated so as dispense the fluid from the dispenser 300 when the dispenser 300 is in the storage state (i.e., detachably coupled to the toothbrush 200). Moreover, because the housing 301 of the dispenser 300 is located within the cavity 280 of the toothbrush 200 when the dispenser 300 is in the storage state, the rotatable actuator 304 is also prohibited from rotating relative to the housing 301 of the dispenser 300.

As can be seen, the proximal edge 251 of the toothbrush 200 and the distal edge 330 of the rotatable actuator 304 correspond to one another in shape. Thus, when the dispenser 300 is in the storage state, the proximal edge 251 of the toothbrush 200 abuts the distal edge 330. In certain embodiments, the proximal edge 251 of the toothbrush 200 and the distal edge 330 of the rotatable actuator 304 are in surface contact with one another and form a continuous interface therebetween. Conceptually, the mating of these edges 330, 251 can also be considered to create the mechanical interference (or keyed cooperation) that prohibits relative rotation between the rotatable actuator 304 and the toothbrush 200.

Figure 10:
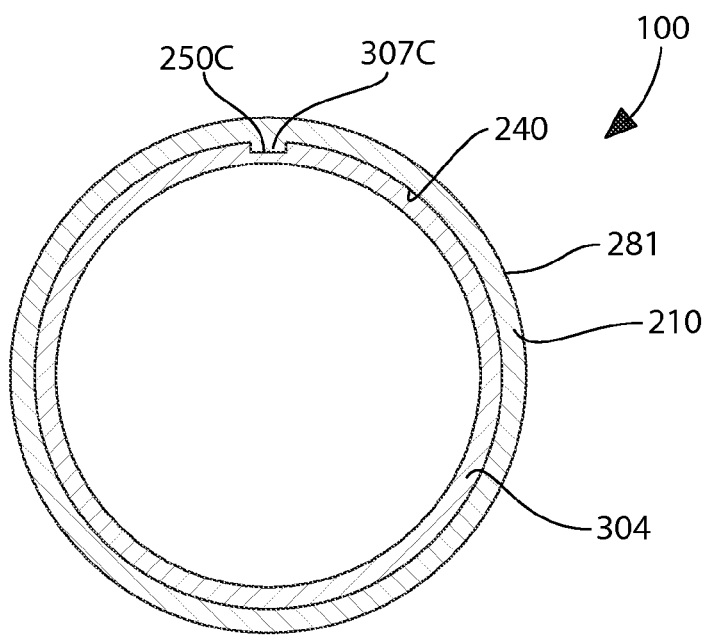
FIG. 10 is a second alternative embodiment of FIG. 9.

While the exemplified embodiment of the rotatable actuator 304 utilizes two members 307A, 307B to create the mechanical interference (or keyed cooperation) between the rotatable actuator 304 and the toothbrush 200, it is to be understood that in certain other embodiments more or less members (or keys) can be used as desired. For example, in certain embodiments, a single member (or key) can be used that mates with a single recess (see e.g., FIGS. 10-11). In other embodiment, more than two members (or keys) can be used that mate with a corresponding number of recesses.

Figure 9:
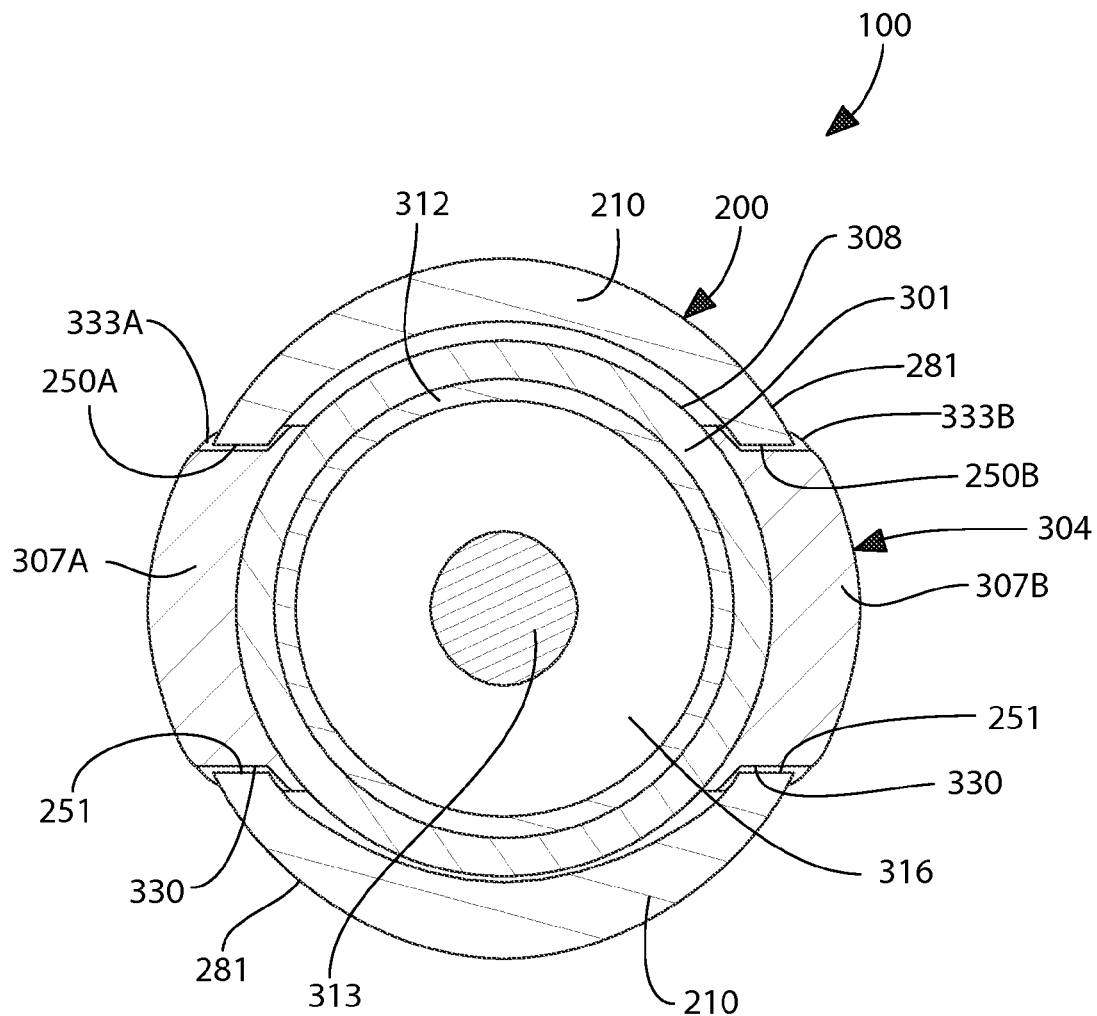
FIG. 9 is a transverse cross-sectional view of the oral care system of FIG. 1 taken along view IV-IV of FIG. 3.

As can best be seen in FIGS. 1 and 9, when the dispenser 300 is in the storage state, the members 307A, 307B protrude radially beyond an outer surface 281 of the toothbrush 200. As a result, the distal edges of the members 307A, 307B form ridges 333A, 333B which provide geometries that a user can grip to slide the dispenser 300 out of the toothbrush 200 from the storage state to the application state. However, in certain other embodiments, the members 307A, 307B may be flush with the outer surface 281 of the toothbrush 200. In even further embodiments, the recesses 250A, 250B may take the form of grooves formed into the inner surface 240 of the toothbrush 200 that do not extend through the entire thickness of the tubular wall of the handle 210 (see e.g., FIG. 11). In such embodiments, the members 307A, 307B would be hidden from view when the dispenser 300 is in the storage state.

Figure 11:
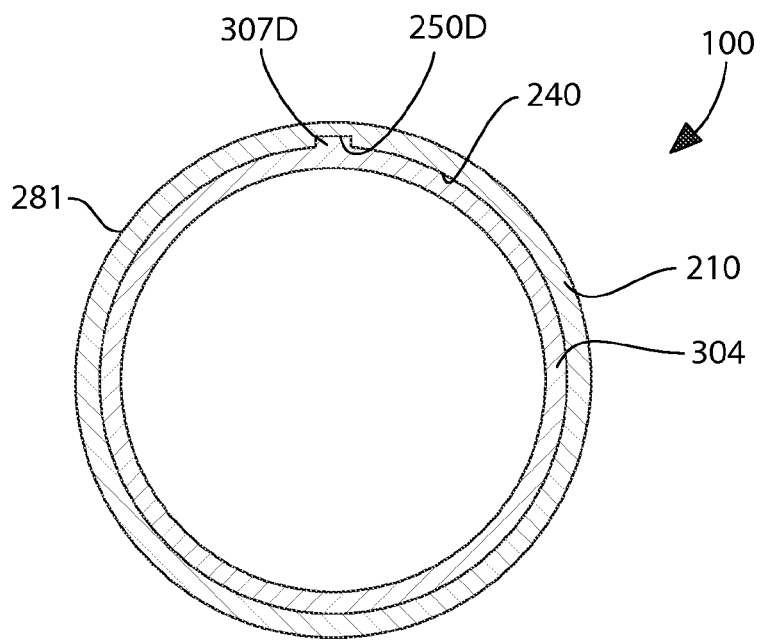
FIG. 11 is a third alternative embodiment of FIG. 9.

Furthermore, while the anti-lock feature of the rotatable actuator 304 is exemplified as the members 307A, 307B, which take the form of elongated arm structures extending from the dome portion 306 in FIGS. 1-10, it is to be understood that the invention is not so limited. In other embodiments, such as that shown in FIG. 10, the anti-lock feature of the rotatable actuator 304 can be a simple protuberance 307C, which can take the form of a ridge, nub or a post that mates with a suitable recess 250C in the handle 210 of the toothbrush 200. Moreover, while all the embodiments of the rotatable actuator 304 have been described above as containing the protuberance 307A-C that mate with a corresponding recessed 250A-C on the handle 210 of the toothbrush, it is to be understood that the location of the protuberance 307A-C and the recesses 250A-C could be swapped in all embodiments. For example, as shown in FIG. 11, the recess(es) 250D could be provided in the rotatable actuator 304 while the protuberance(s) 307D could be provided on the handle 210 of the toothbrush 200. Based on the present disclosure, those skilled in the art will appreciate that the keyed cooperation (or mechanical interference) between the rotatable actuator 304 and the toothbrush 200 can be effectuated by a large number of geometries and mating structures.

In certain other embodiments, a portion of the rotatable actuator 304 may be nested within the cavity 280 of the handle 210 of the toothbrush 200. In such embodiments, the protuberance (or recess) of the rotatable actuator 304 that acts as the anti-rotation feature would simply be located on an outer surface of the rotatable actuator 304 and would not extend over the housing 301 of the dispenser 300.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

While the foregoing description and drawings represent the exemplary embodiments of the present invention, it will be understood that various additions, modifications and substitutions may be made therein without departing from the spirit and scope of the present invention as defined in the accompanying claims. In particular, it will be clear to those skilled in the art that the present invention may be embodied in other specific forms, structures, arrangements, proportions, sizes, and with other elements, materials, and components, without departing from the spirit or essential characteristics thereof. One skilled in the art will appreciate that the invention may be used with many modifications of structure, arrangement, proportions, sizes, materials, and components and otherwise, used in the practice of the invention, which are particularly adapted to specific environments and operative requirements without departing from the principles of the present invention. The presently disclosed embodiments are therefore to be considered in all respects as illustrative and not restrictive, the scope of the invention being defined by the appended claims, and not limited to the foregoing description or embodiments.

What is claimed is:

1. An oral care system comprising:
   an oral care implement;
   a dispenser comprising a reservoir containing a fluid and an actuator for dispensing the fluid from the dispenser; and
   the dispenser alterable between: (i) a storage state such that a mechanical interference between a portion of the actuator and a portion of the oral care implement prohibits actuation of the actuator relative to the oral care implement; and (ii) an application state in which a user can actuate the actuator to dispense the fluid from the dispenser.

2. The oral care system according to claim 1 wherein a handle of the oral care implement comprises a cavity, and wherein a portion of the dispenser is located within the cavity in the storage state.

3. The oral care system according to claim 2 wherein a majority of a length of the dispenser is located within the cavity in the storage state.

4. The oral care system according to claim 2 wherein the actuator protrudes from the cavity of the handle in the storage state.

5. The oral care system according to claim 2 wherein the cavity extends along a longitudinal axis of the handle and terminates at an opening at a proximal end of the handle, the opening forming a passageway into the cavity through which a portion of the dispenser can be slid, the actuator forming a longitudinal extension of the handle.

6. The oral care system according to claim 2 wherein only the actuator of the dispenser protrudes from the cavity when the dispenser is in the storage state.

7. The oral care system according to claim 1 wherein the actuator comprises a dome portion, the dome portion forming the longitudinal extension of the handle.

8. The oral care system according to claim 1 wherein the mechanical interference between the portion of the actuator and the portion of the oral care implement is a keyed cooperation between the portion of the actuator and the portion of the oral care implement.

9. The oral care system according to claim 1 wherein one of the portion of the actuator or the portion of the oral care implement comprises a recess while the other one of the portion of the actuator or the portion of the oral care implement comprises a protuberance that mates with the recess when the dispenser is in the storage state.

10. The oral care system according to claim 9 wherein the portion of the actuator comprises the protuberance and the portion of the oral care implement comprises the recess.

11. The oral care system according to claim 10 wherein the protuberance of the actuator protrudes beyond an outer surface of the oral care implement when the dispenser is in the storage state to form a ridge which the user can grip to slide the dispenser from the storage state to the application state.

12. The oral care system according to claim 2 wherein the cavity extends along a longitudinal axis of the handle and terminates at an opening defined by a proximal edge of the handle, the actuator comprising a distal edge, and wherein when the dispenser is in the storage state, the distal edge of the actuator abuts the proximal edge of the handle so as to create the mechanical interference that prevents actuation of the actuator.

13. The oral care system according to claim 12 wherein the distal edge of the actuator and the proximal edge of the handle undulate in a corresponding manner.

14. The oral care system according to claim 2 wherein the dispenser further comprises an elongated housing comprising the reservoir and an applicator located at a distal end of the elongated housing, the actuator located at a proximal end of the housing, and wherein actuation of the actuator relative to the elongated housing dispenses the fluid from the reservoir to the applicator; the cavity extending along a longitudinal axis of the handle and terminating at an opening defined by a proximal edge of the handle; and the elongated housing of the dispenser located within the cavity of the handle and the actuator protruding from the proximal edge of the handle to form a longitudinal extension of the handle in the storage state.

15. The oral care system according to claim 2 wherein the dispenser is entirely removed from the cavity and separated from the oral care implement in the application state.

16. The oral care system according to claim 2 wherein the dispenser is secured within the cavity in the storage state due to an interference fit between an outer surface of the elongated housing of the dispenser and an inner surface of the handle that forms the cavity.

17. The oral care system according to claim 14 wherein the actuator comprises a dome portion that forms the longitudinal extension of the handle in the storage state and at least one prong extending from the dome portion over an outer surface of the housing, the prong nesting within a recess formed in the proximal edge of the handle when the dispenser is in the storage state.

18. An oral care system comprising:
   an oral care implement comprising:
      a handle;
      an anti-actuation feature; and
      a head;
   a dispenser comprising:
      a housing having a reservoir containing a fluid;
      a dispensing orifice located at a distal end of the housing;
      a actuator having an anti-actuation feature, the actuator located at a proximal end of the housing, wherein upon actuation of the actuator, the fluid from the reservoir is dispensed via the dispensing orifice; and
   the dispenser alterable between: (i) a storage state such that the anti-actuation features of the oral care implement and the actuator mechanically mate to prohibit actuation of the actuator; and (ii) an application state in which a user can actuate the actuator to dispense the fluid from the dispenser, the dispenser being detached from the oral care implement.

19. The oral care system according to claim 18 wherein the anti-actuation feature of one of the actuator or the oral care implement comprises a recess while the anti-actuation feature of the other one of the actuator or the oral care implement comprises a protuberance that mates with the recess when the dispenser is in the storage state.

20. The oral care system according to claim 19 wherein when the dispenser is altered from the application state to the storage state, the protuberance slides into the recess.

21. The oral care system according to claim 18 wherein the handle comprises a cavity extending along a longitudinal axis of the handle and terminating at an opening at a proximal end of the handle, and wherein the housing of the dispenser is located within the cavity and the actuator forms a longitudinal extension of the handle in the storage state.

22. The oral care system according to claim 21 wherein the actuator comprises a dome portion, the dome portion forming the longitudinal extension of the handle, the anti-actuation feature of the actuator comprising at least one prong that extends from the dome portion toward the distal end of the housing, the anti-actuation feature of the oral care implement comprising at least one recess in the handle, the prong of the actuator mating with the recess of the handle when the dispenser is in the storage state to prohibit actuation of the actuator.

23. The oral care system according to claim 18 wherein the anti-actuation feature of the actuator comprises a distal edge of the actuator and wherein the anti-actuation feature of the oral care implement comprises a proximal edge of the handle of the oral care implement.

24. The oral care system according to claim 18 wherein the dispenser is separated from the oral care implement in the application state.

25. The oral care system according to claim 18 wherein the handle comprises a cavity, at least a portion of the housing of the dispenser located within the cavity of the handle when the dispenser is in the storage state, and wherein dispenser is secured within the cavity in the storage state due to an interference fit between an outer surface of the housing of the dispenser and an inner surface of the handle that forms the cavity.

26. An oral care system comprising:
an oral care implement;
a dispenser comprising a reservoir containing a fluid and anactuator for dispensing the fluid from the dispenser;
the dispenser alterable between: (i) a storage state in which the dispenser is detachably coupled to the oral care implement; and (ii) an application state in which the dispenser is separated from the oral care implement; and
one of the oral care implement or the dispenser comprising a key and the other of the oral care implement or the dispenser comprising a recess, and wherein the key mates with the recess when the dispenser is in the storage state so as to prohibit actuation of the actuator.

27. The oral care system according to claim 26 wherein the dispenser comprises a housing containing the reservoir, an dispensing orifice located at a distal end of the housing, and the actuator at a proximal end of the housing, and wherein the oral care implement comprises a cavity, the elongated housing and the dispensing orifice of the dispenser located within the cavity when the dispenser is in the storage state.

28. The oral care system according to claim 27 wherein the cavity extending along a longitudinal axis of the handle and terminates at an opening at a proximal end of the handle.

29. The oral care system according to claim 28 wherein the actuator comprises a dome portion, the dome portion forming the longitudinal extension of the handle.

* * * * *